United States Patent [19]

Fineman

[11] Patent Number: 4,803,470
[45] Date of Patent: Feb. 7, 1989

[54] SUBSTANCE DETECTOR DEVICE

[76] Inventor: Howard Fineman, 13305 Lockgate Pl., Herndon, Va. 22071

[21] Appl. No.: 854,801

[22] Filed: Apr. 23, 1986

[51] Int. Cl.$^4$ .............................................. G08B 19/02
[52] U.S. Cl. ...................................... 340/583; 356/136
[58] Field of Search ............... 356/128, 135, 136, 137; 340/583

[56] References Cited

U.S. PATENT DOCUMENTS

| 2,355,014 | 8/1944 | Schorn . | |
|---|---|---|---|
| 2,359,787 | 10/1944 | Peters et al. . | |
| 3,045,223 | 7/1962 | Kapany et al. . | |
| 3,323,410 | 6/1967 | Waters | 356/136 |
| 3,487,069 | 12/1969 | Maselli . | |
| 3,540,025 | 11/1970 | Levin et al. . | |
| 3,751,672 | 8/1973 | Michel et al. . | |
| 3,932,038 | 1/1976 | Schweizer et al. . | |
| 3,947,131 | 3/1976 | Karl . | |
| 4,306,805 | 12/1981 | Arrington | 356/136 |
| 4,379,227 | 4/1983 | Kovacs . | |
| 4,422,714 | 12/1983 | Benoit et al. | 356/136 |
| 4,538,064 | 8/1985 | Kovacs . | |

FOREIGN PATENT DOCUMENTS

| 0071143 | 2/1983 | European Pat. Off. | 356/136 |
|---|---|---|---|
| 2807805 | 10/1978 | Fed. Rep. of Germany | 356/136 |

Primary Examiner—F. L. Evans
Attorney, Agent, or Firm—Foley & Lardner, Schwartz, Jeffery, Schwaab, Mack, Blumenthal & Evans

[57] ABSTRACT

The substance detection device comprises a transparent element and a light source for transmitting light through the transparent element onto a polished surface of the element. A pair of photodetectors are positioned for detecting intensity of light reflected from the polished surface and a circuit is provided for determining a difference in detected reflected light intensity on the photodetectors to determine a change in the critical angle of an optical interface at the polished surface.

18 Claims, 5 Drawing Sheets

FIG. 7a.
FIG. 7b.
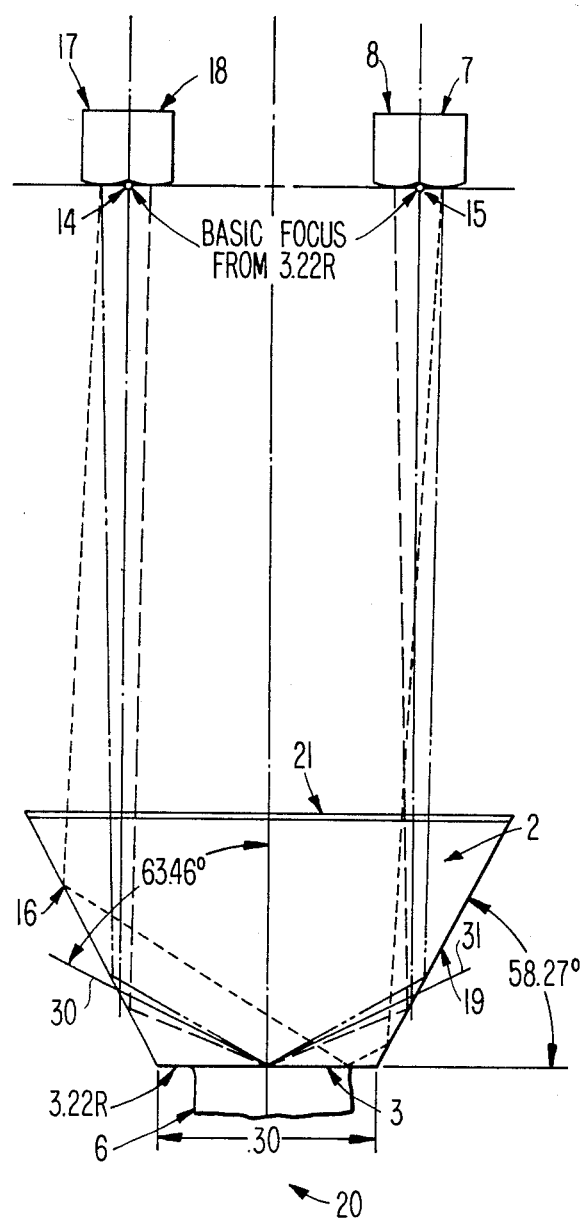
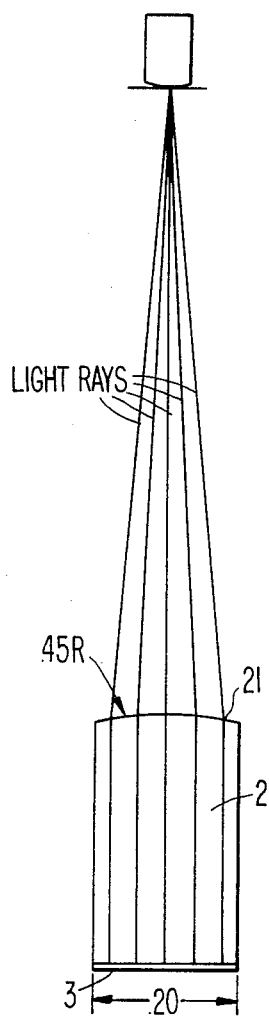

SUBSTANCE DETECTOR DEVICE

BACKGROUND OF THE INVENTION

Field of the Invention

The present invention relates to a device for detecting the presence of one or a plurality of specific substances and for producing a suitable output signal upon the detection thereof.

Related Art

Photocells have often been used in substance detecting systems. U.S. Pat. No. 3,487,069 discloses a refractometer with compensating photocells. A light beam is reflected from a prism-liquid interface onto three groups of photocells. One of the photocells measures light at the angle of reflection and the other photocells compensate for unwanted light which is reflected onto the measuring photocell. A difference in light intensity falling on the photocells causes a varying output current which is detected by a microammeter. The photocells are used for detecting the edge of a light beam, i.e., a sudden change in light intensity that occurs at the critical angle. When liquids with varying indices of refraction are used, the critical angle changes. As the index of refraction of the liquid increases, the critical angle also increases, and the bright area decreases. Thus, the output of the photocells is effectively decreased. The "beam edge" is detected by measuring the electrical difference in output between the reference photocell and the pair of photocells. This measurement is approximately proportional to the difference in illumination between the cells. Accordingly, the electrical output, which is proportional to the deflection to the microammeter, is susceptible to errors from stray light, drifting of characteristics in system components, and fluctuations in supply voltage.

U.S. Pat. Nos. 2,355,014, 2,359,787, 3,540,025 and 3,751,672 disclose single photocell devices which utilize the principle of total reflection and a single photocell to indicate the presence of a substance or its index of refraction. These systems operate on the principle that the presence of a substance on an optical interface would result in a larger critical angle than with air. This increases the area having a lower reflection intensity and indicates the presence of the detected substance by a decreased light intensity on the photocell. This approach is particularly prone to erroneous readings, because it is susceptible to light variations, dirt in the optical system, aging of components, etc. Further, erroneous results will likely be produced for substances of slightly different indices of refraction, such as water and ice.

U.S. Pat. Nos. 3,045,223, 3,932,038, 3,94,131, 4,379,227 and 4,538,064 utilize the darkening effect or light-type effect of a substance to detect its presence. This effect is used to change the intensity of light falling on a photocell from some light source.

SUMMARY OF THE INVENTION

One object of the present invention is to provide a substance detection device which can accurately and reliably determine the presence of a particular substance on a surface.

A further object of the present invention is to provide a substance detection device which can be used in connection with an aircraft or road surface to detect the presence of ice.

A still further object of the present invention is to provide a substance detection device which can be produced in a compact configuration so as to fit into confined spaces.

Yet another object of the present invention is to provide a substance detection device which can be formed of conventional optical elements.

In accordance with the above and other objects, the present invention is a substance detection device comprising an optically transparent element having a polished surface. A first light source is positioned for transmitting light through the optically transparent element to the polished surface and a pair of photodetectors are positioned to detect an intensity of light reflected from the polished surface. Circuits are provided for determining a difference in detected reflected light intensity on the pair of photodetectors to determine a change in critical angle of an optical interface at the polished surface.

According to the invention, the photodetectors may be positioned on opposite sides of a critical angle determined in accordance with a substance to be detected on the polished surface.

Furthermore, a plurality of pairs of photodetectors may be provided in order to detect a plurality of different substances.

In one embodiment, the polished surface is a section of a substantially cylindrically shaped structure and one of the photodetectors is positioned at a first position on an axis of the polished surface and the other of the pair of photodetectors is positioned at a second position on the axis of the polished surface.

In another embodiment, the polished surface is a section of a substantially elliptically shaped structure. A light source is positioned on a first side of a focus of the polished surface and a second light source is positioned on a second side of the focus of the polished surface.

BRIEF DESCRIPTION OF THE DRAWINGS

The above and other objects of the present invention will become more readily apparent as the invention becomes more fully understood from the detailed description to follow, reference being had to the accompanying drawings in which like reference numerals represent like parts throughout and in which:

FIG. 5b is an end elevational view of the embodiment of FIG. 5a;

FIG. 6b is an end elevational view of the embodiment of FIG. 6a;

FIG. 7a is a side elevational view of a fourth embodiment of the present invention; and FIG. 7b is an end elevational view of the embodiment of FIG. 7a.

DETAILED DESCRIPTION OF THE PREFERRED EMBODIMENTS

Figure 1B:
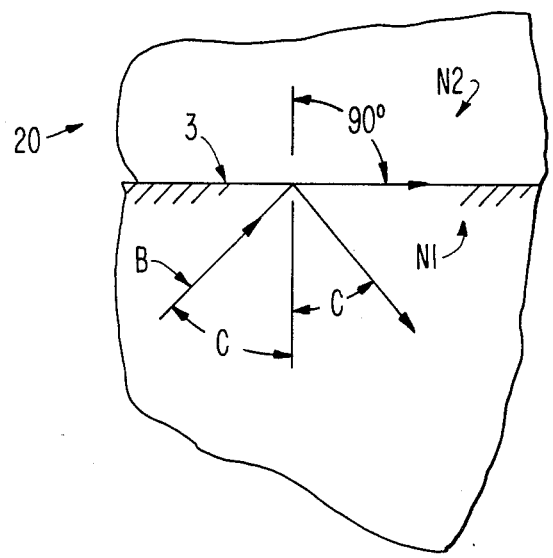
FIGS. 1a and 1b are schematic diagrams illustrating the principles of the present invention.
Figure 1A:
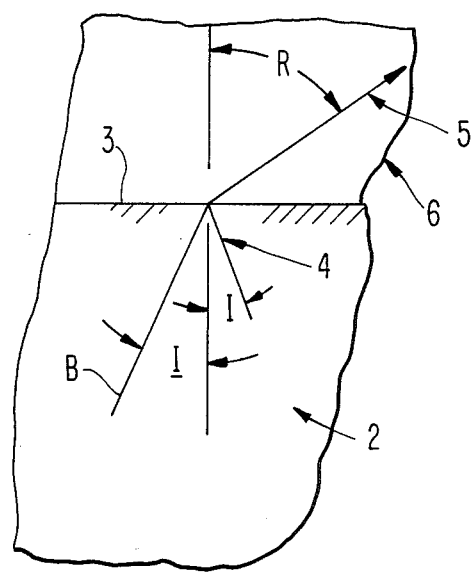

Referring now to the drawings, FIG. 1a illustrates a light beam B passing from a first optical medium 2 through a polished surface 3 and into a second optical medium 6. The light beam B hits the polished surface 3 at an incident angle I. Some of the light is transmitted along beam 5 at an angle R into the second optical medium 6. Some of the light is reflected off of the polished surface 3 at an angle I and back into the first optical medium 2 as beam 4. Snell's law defines the relation between the incident and refracted angles as follows:

$$n_2 \sin(I) = n_6 \sin(R)$$

where $n_2$ and $n_6$ are the indices of refraction of the first and second optical mediums, respectively, and I and R are the incident and refracted angles, respectively. The critical angle is defined as the incident angle at which no light is transmitted to the second optical medium. The critical angle, C, is reached where the refracted angle R equals 90°, as shown in FIG. 1b. Every optically transparent substance has a specific index of refraction. If the light ray emerges into a particular transparent substance, the critical angle can be detected if the indices of refraction of the two substances are known. Generally, the critical angle can be detected by use of an arrangement including a light source, photodetectors, and electronic circuitry.

Figure 2:
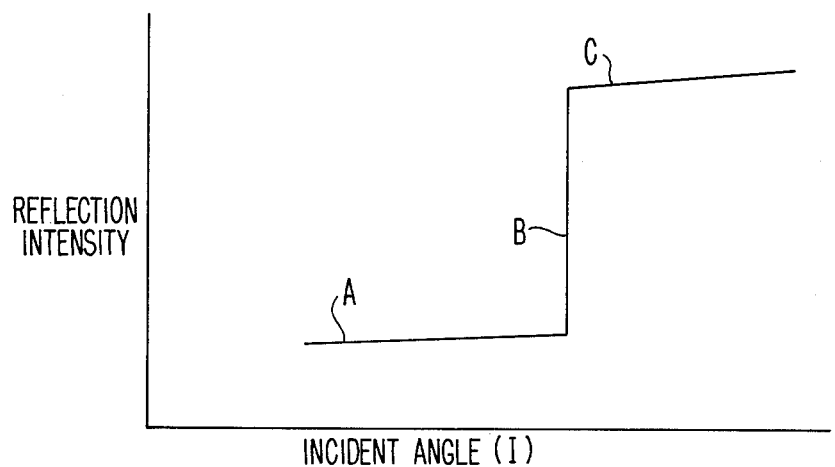
FIG. 2 is a graphical representation with incident angle indicated on the abscissa and reflection intensity indicated on the ordinate showing the difference in reflected intensity as the incident angle varies relative to the critical angle.

FIG. 2 illustrates the relationship between the intensity of the reflected beam and the incident angle. As can be seen from the graph, the intensity of the reflected beam 4 increases slightly with the critical angle, as shown in section A of the graph, until the critical angle is reached. At the critical angle, a sharp change in reflected intensity occurs, as shown by section B. Above the critical angle, the reflected intensity is the greatest, as shown by section C. This difference in intensity can be easily detected by photodetectors aligned on either side of the critical angle.

Figure 3:
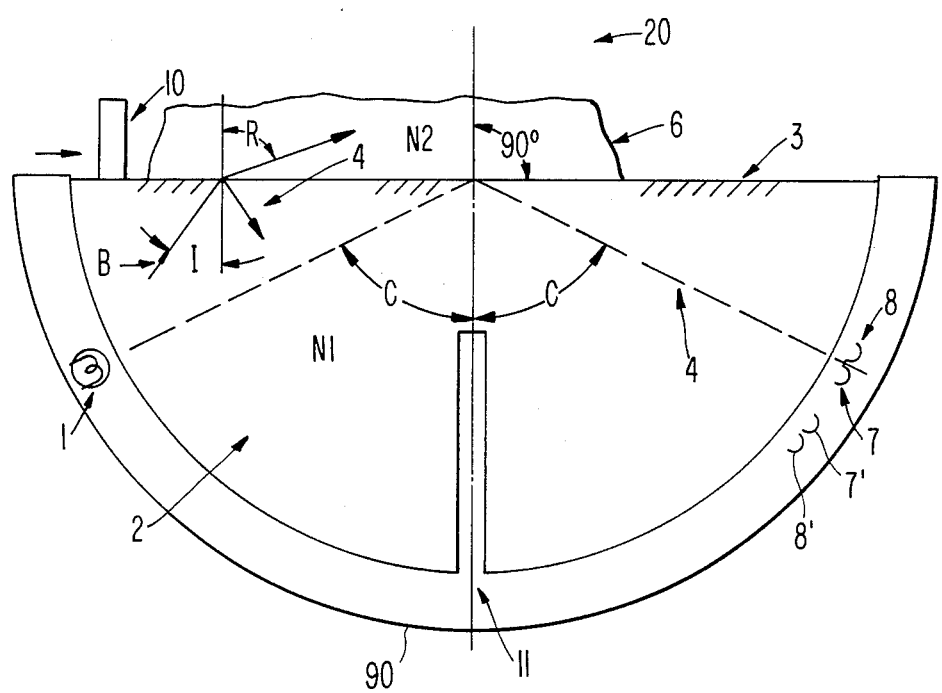
FIG. 3 is a schematic representation of one embodiment of the present invention.

Referring to FIG. 3, an arrangement including such photodetectors is shown. Like components to FIG. 1 are designated with like numerals, and a discussion of these elements will be omitted. Light source 1 illuminates the polished surface 3 of optical medium 2. Photodetectors 7 and 8 are positioned on either side of the critical angle C, calculated for the presence of a substance 6 on the surface 3. In the present case, the substance is assumed to be ice. The difference between the amount of light received by the photodetectors is measured. Accordingly, where the incident light beam impinges on surface 3 at an angle less than the critical angle, as shown by beam B in FIG. 3, the reflection intensity will be that measured on part A of the graph shown in FIG. 2. Where light impinges on the polished surface 3 at an angle greater than the critical angle the reflected intensity will correspond to that part of the curve denoted by C in FIG. 2. Since photodetectors 7 and 8 are positioned on opposite sides of the critical angle, there will be a sharp difference in their outputs.

The index of refraction of optical medium 2 is known. This material can be, for example, acrylic having an index of refraction of 1.49 giving a critical angle of 42.2 degrees. With ice on the surface 3, the critical angle increases to about 63.5 degrees. The photodetectors 7 and 8 are placed on either side of the 63.5 degree critical angle. Accordingly, when ice collects on the polished surface 3, the amount of light received by the two photodetectors will be substantially different. However, where no ice 6 is present on the polished surface 3, the photodetectors 7 and 8 will receive approximately equal amounts of reflected light. Accordingly, the presence of ice 6 is identified by measuring the difference between the amount of light received by photodetectors 7 and 8. This difference can be generated into a signal by appropriate electrical circuitry, and the signal can be used directly to operate a passive electrical meter, or the signal can be amplified and transformed by suitable known electronic circuits for purposes of producing a control output to actuate desired remote devices using well known electronic principles.

In order to prevent light from source 1 from directly illuminating photocells 7 and 8 a shield or blocking element 11 is interposed between source 1 and the photocells 7 and 8.

Figure 4:
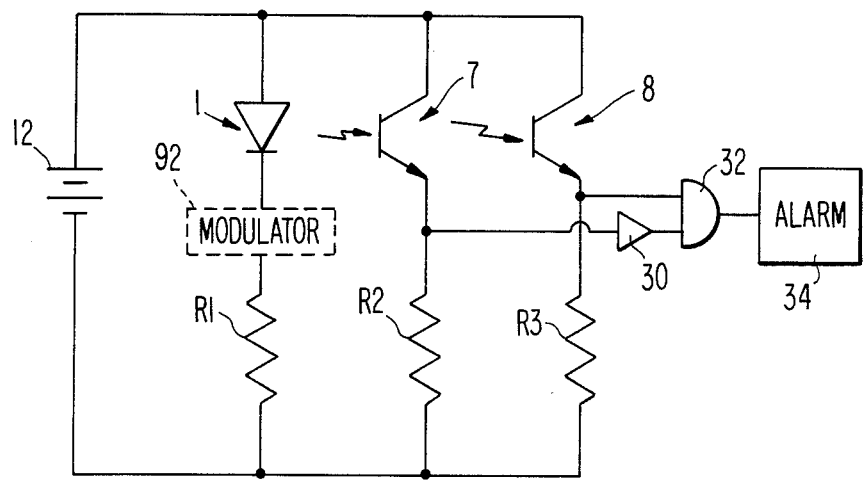
FIG. 4 is a schematic diagram of a circuit to be used with the present invention.

Referring to FIG. 4, a basic circuit configuration for the embodiment of FIG. 3 is shown. Light source 1, which may be a light emitting diode, is positioned as shown in FIG. 3 and is electrically connected to a battery 12 and photodetectors 7 and 8 via resistor R1, R2, and R3, respectively. A logic circuit is connected across the outputs of photodetectors 7 and 8 to determine the presence of ice. The logic circuit comprises an inverter 30 connected to the output of photodetector 7 and an AND gate 32 connected to the outputs of inverter 30 and photodetector 8. An alarm circuit 34 may be connected to the output of the AND gate 32. In place of the logic circuit, a comparator may be used.

In operation, when there is no ice 6 present on surface 3, photodetectors 7 and 8 will be illuminated equally and there will be no output from AND gate 32. When ice forms on surface 6, photodetector 8 will produce a high output and photodetector 7 will produce a low output. By inverting the low output of photodetector 7 in inverter 30, two high signals are presented to AND gate 32 so that a high output is produced by this gate. The high output of gate 32 actuates alarm 34.

The present invention is ideally suited for detecting ice on airplane wings, road surfaces, and the like. The surface 3 is mounted flush with the airplane wing or road surface and the acrylic member 2 is mounted inside of the wing or road surface.

In order to optimize the system as shown in FIGS. 3 and 4, it is desired to maximize the increase in light intensity shown along portion B of the curve in FIG. 2. This can be accomplished by using an optically focused or point source of light. In this manner, substances with only a slight difference in indices of refraction can be differentiated from one another.

Also, an array of N light detectors may be used to determine the point of maximum light change corresponding to portion B of the curve in FIG. 2. For example, a second pair of photodetectors is shown in phantom in FIG. 3 at 7' and 8'. Alternatively, the point of maximum light change can also be detected by adjusting the position of the two light detectors 7 and 8 or the light source 1 parallel to their adjacent optical surfaces. Either of these techniques can be used to detect a plurality of different substances by determining the exact critical angle and comparing this critical angle with known critical angles of various substances.

The present invention can be used to identify any number of materials which have a lower index of refraction than the transparent material 2. For example, water, gasoline, alcohol, crystals of salt, etc. may be detected.

Figure 5A:
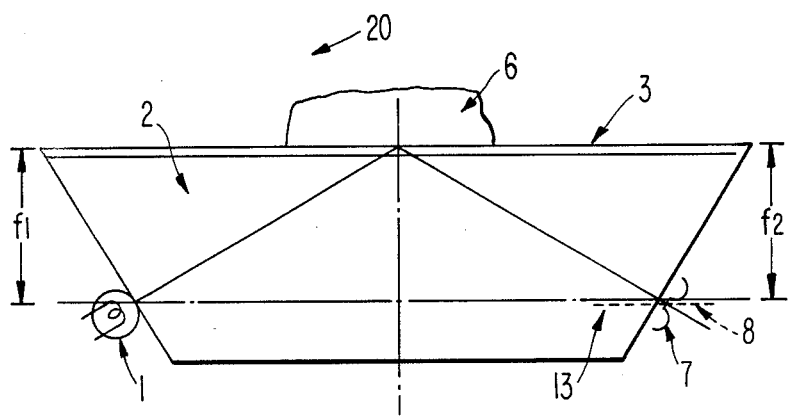
FIG. 5a is a side elevational view of a second embodiment of the present invention.
Figure 5B:
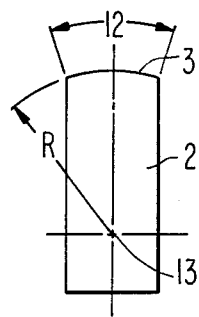

Referring to FIGS. 5a and 5b, a second embodiment of the invention is shown. Like components are designated by like reference numerals, and a discussion of these elements will be omitted.

In FIG. 5a, the polished surface 3 is formed in the shape of a section of a cylinder. This cylindrical shape is shown in FIG. 5b which is an end elevational view of the transparent block 2. Light source 1 and photodetectors 7 and 8 are placed at foci F1 and F2 of the curved surface. These occur at the center of curvature or cylindrical axis 13. By using a curved surface, any defects or imperfections in the polished surface 3 or granularity or non-uniformity in the substance 6 is integrated (or averaged) over a significantly greater area. This occurs because the wide band of light 12 (FIG. 5b) which extends across the polished surface 3 is focused by the curved polished surface 3 into a line 13 along the axis of the cylinder.

Figure 6A:
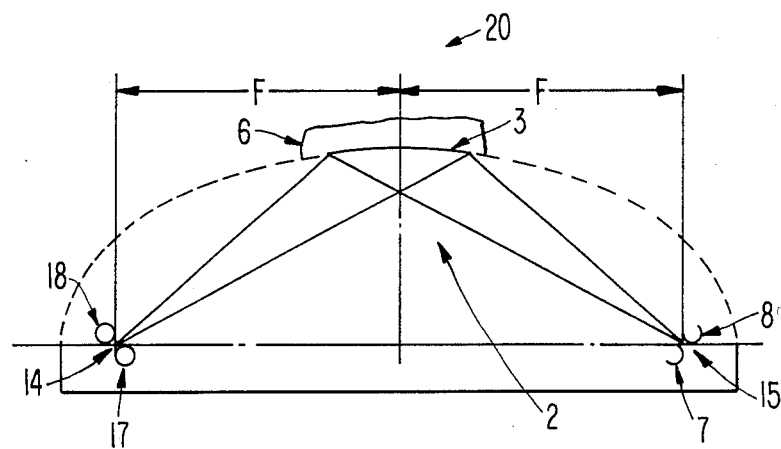
FIG. 6a is a side elevational view of a third embodiment of the present invention.
Figure 6B:
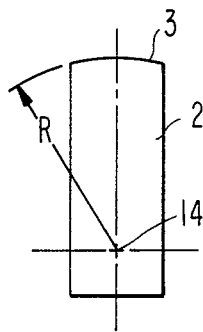

The curvature of the polished surface can also be in the shape of an ellipsoid or ellipse of revolution, as shown in FIGS. 6a and 6b. The embodiment in FIGS. 6a and 6b employs two light sources 17 and 18. The two light sources 17 and 18 are disposed on either side of a focus 14 of the curved surface. A pair of photodetectors 7 and 8 are placed opposite the light sources on opposite sides of a second focus 15 of the curved surface. The curvature of the ellipsoid is designed to conform to the following equation:

$$F/R = \tan(C)$$

where F is the focal distance of the ellipsoid, R is the minor axis of the ellipsoid, and C is the critical angle calculated for the substance of interest on surface 3.

All of the light from light source 17 is focused onto photodetector 7; whereas all of the light from light source 18 is focused onto photodetector 8. The area of surface 3 is chosen such that the angle of incidence of the rays from light source 17 is less than that of the rays from light source 18 over the entire surface 3. The remainder of the outer surface of element 2 can be roughened to prevent reflection. Thus, when substance 6 is present, causing the critical angle to be between the angle of incidence of light source 17 and the angle of incidence of light source 18, some of the light from source 17 will be refracted whereas all of the light from source 18 will be reflected. Consequently, there will be a difference in illumination of the photodetectors 7 and 8. On the other hand, when substance 6 is absent, all of the light from both sources will be reflected. Thus, in this case, the photodetectors 7 and 8 are equally illuminated. A circuit such as that shown in FIG. 4 can be used to indicate the presence of substance 6.

The advantage of the embodiment of FIGS. 6a and 6b is that virtually all of the reflected light is integrated across the entire surface of the surface 3 and focused onto one of the photodetectors. Light intensity is increased in this manner. Thus, undesirable side effects from surface imperfections, defects, granularities, and the like, are even further reduced than is possible with the embodiment of FIG. 5.

Referring to FIGS. 7a and 7b, a fourth embodiment of the invention is shown. Like components are designated by like numerals and a discussion of these elements will be omitted. The polished surface 3 shown in FIGS. 7a and 7b is a section of an ellipse. In order to facilitate production, the ellipse can be approximated by a cylinder having the same basic radius. The polished surface is 0.30 inches in length. The foci of ellipse 3 are located on lines 30 and 31 which are at 63.46° in this example. However, in order to conserve space, rather than locate the light sources and photodetectors at the foci, reflecting surfaces 16 and 19 are provided. Surfaces 16 and 19 are at an angle of 58.27° to the horizontal to cause points 14 and 15 to act as foci of the ellipse as reflected through surfaces 16 and 19. Light sources 17 and 18 are placed on opposite sides of the basic focus point 14 and direct light rays to transparent element 2. The upper surface 21 (in the drawings) of element 2 is a secion of a cylinder with a radius of curvature which is sufficient to cause the rays from light sources 17 and 18 to travel in parallel paths in element 2, as shown in FIG. 7b. The light rays from sources 17 and 18 are then reflected from reflecting surface 16. The light from light sources 17 and 18 then impinges on the surface 3. The light reflected from surface 3 hits the second reflecting surface 19. Reflecting surface 19 and curved surface 21 focus the outgoing rays onto photodetectors 7 and 8 which are positioned on opposite sides of focus 15. Light from source 17 is focused onto photodetector 7 and light from source 8 is focused onto photodetector 8. As can be seen in FIG. 7a, the rays from source 17 reflect off surface 16 and strike surface 3 with a greater angle of incidence than the light rays from source 18. Accordingly, a substance 6 which causes a critical angle between the angle of incidence of light from source 17 and the angle of incidence of light from source 18 will create a difference in reflected intensity to be sensed by photodetectors 7 and 8. This difference is signalled by a circuit such as that of FIG. 4.

The embodiment of FIGS. 7a and 7b produces essentially the same results as the embodiment of FIGS. 6a and 6b but is more compact and is easier to produce. In the embodiment of FIGS. 7a and 7b, an elliptical surface in combination with a cylindrical surface serves to focus and integrate the rays. These surfaces are easier to produce than the ellipsoidal surface of FIGS. 6a and 6b. Also, the light sources 17 and 18 and the photodetectors 7 and 8 can be conveniently positioned by providing reflecting surfaces 16 and 19 at the appropriate angle.

The values disclosed in the embodiment of FIGS. 7a and 7b are for illustrative purposes only, and it would be apparent to those skilled in the art that the same result may be achieved using other values.

It should be understood that by moving the light sources and photodetectors off of the foci in the embodiments of FIGS. 5, 6a, 6b, 7a and 7b, perfect focusing of the light beams will not be achieved. This does not cause any problem as long as the distance separating the light sources from each other and the distance separating the photodetectors from each other is greater than the blur spots created by the focused light so that the light focused on one photodetector does not overlay onto the other photodetector.

In all of the above embodiments, light detectors 7 and 8 can become contaminated by external light, which causes a decrease in the system signal to noise ratio. Further, this increases the probability of an erroneous output. These drawbacks can be alleviated by roughening the inactive internal surfaces and painting them a flat, black color. Further, an optical barrier can be placed between the light source and the photocells to prevent direct illumination (as discussed above relative to FIG. 3). Additionally, the entire optical system can be sealed against leakage of external light into the system, with the exception of the region wherein a substance is to be detected as shown in FIG. 3 by shield 90. The signal-to-noise ratio of the system can be further improved by modulating the light source at a constant frequency and designing the light detector circuit to amplify and transmit only the predetermined constant frequency. This is shown in FIG. 4 by modulator 92 in phantom. Finally, the light source and photodetectors can be made operable within only a narrow band of light, such as ultraviolet or infrared.

While several embodiments of the invention have been described it will be understood that it is capable of further modification, and this application is intended to cover any variations, uses, or adaptations of the invention, following in general the principles of the invention and including such departures from the present disclosure as come within knowledge or customary practice in the art to which the invention pertains, and this may be applied to the essential features hereinbefore set forth and falling within the scope of the invention or the limits of the appended claims.

What is claimed is:

1. A substance detection device comprising:
   an optically transparent element having a polished surface;
   a first light source for transmitting light through said optically transparent element to said polished surface;
   a pair of photodetectors positioned on opposite sides of a critical angle determined in accordance with a substance the presence of which is to be detected on said polished surface for detecting an intensity of light reflected from said polished surface of said optically transparent element, said photodetectors being positioned such that one of said photodetectors is fully illuminated by light reflected at said critical angle when said substance is present on said surface and the other of said photodetectors is not illuminated by light when said substance is present on said surface;
   means for determining a difference in detected reflected light intensity on said pair of photodetectors to determine a change in critical angle of an optical interface at said polished surface and outputting an on/off alarm signal indicative of the presence of said substance on said polished surface when said difference reaches a predetermined amount indicative one of said photodetectors being fully illuminated and the other of said photodetectors not being illuminated.

2. The substance detection device of claim 1, wherein a plurality of pairs of photodetectors are provided for detecting the presence of different substances and wherein one of said determining means is provided for each of said pairs of photodetectors.

3. The substance detection device of claim 1, wherein said polished surface is substantially flat.

4. The substance detection device of claim 1, wherein said polished surface is a section of a cylinder; and
   wherein said light source is positioned to project light from a first point along an axis of said polished surface, said pair of photodetectors is spaced from said light source along said axis and one of said pair of photodetectors is positioned at a first position relative to said axis of said polished surface and the other of said pair of photodetectors is positioned at a second position relative to said axis of said polished surface.

5. The substance detection device of claim 1, further comprising a second light source; and
   wherein said polished surface is a section of a substantially elliptically shaped structure; and
   wherein said first light source is positioned on a first side of a focus of said polished surface and said second light source is positioned on a second side of the focus of said polished surface.

6. The substance detection device of claim 5, wherein a ratio of a focal distance of said polished surface to a minor axis of said polished surface is substantially equal to a tangent of the critical angle of said optically transparent element.

7. The substance detection device of claim 1, further comprising totally reflecting flat surfaces disposed along side portions of said optically transparent element so that incoming and outgoing light rays are reflected.

8. A substance detection device of claim 1, further comprising a barrier means, positioned between said first light source and said pair of photodetectors for preventing direct illumination of said pair of photodetectors means.

9. The substance detection device of claim 1, further comprising a sealing means for preventing entry of external light into the optically transparent element.

10. The substance detection device of claim 1, further comprising a means for modulating said first light source at a substantially constant frequency; and
    wherein said pair of photodetectors are responsive only to the substantially constant frequency.

11. The substance detection device of claim 1, wherein said first light source and said pair of photodetectors operate only in a predetermined narrow frequency band.

12. The substance detection device of claim 1 wherein said polished surface is a section of an ellipsoid.

13. The substance detection device of claim 1 wherein said optically transparent element includes a generally cylindrical surface for focusing light rays onto said polished surface.

14. The substance detection device of claim 13 wherein said polished surface is generally elliptical.

15. The substance detection device of claim 1 wherein said determining means comprises an inverting circuit connected to an output of one of said photodetectors and an AND circuit having inputs connected, respectively, to an output of the other of said photodetectors and to an output of said inverting circuit, and an alarm circuit connected to receive an output of said AND circuit.

16. The substance detection device of claim 15 wherein each of said photodetectors is connected in series with a resistance and the series combinations of said photodetectors and resistors are connected in parallel to each other.

17. The substance detection device of claim 1 wherein said critical angle is about 63.5 degrees.

18. The substance detection device of claim 1 wherein said substance is ice.

* * * * *